(12) United States Patent
Tsuboi (10) Patent No.: US 10,379,327 B2
(45) Date of Patent: Aug. 13, 2019

(54) SCANNING MICROSCOPE

(71) Applicant: OLYMPUS CORPORATION, Hachioji-shi, Tokyo (JP)

(72) Inventor: Hidenori Tsuboi, Kanagawa (JP)

(73) Assignee: OLYMPUS CORPORATION, Tokyo (JP)

(*) Notice: Subject to any disclaimer, the term of this patent is extended or adjusted under 35 U.S.C. 154(b) by 119 days.

(21) Appl. No.: 15/608,342

(22) Filed: May 30, 2017

(65) Prior Publication Data

US 2017/0363848 A1 Dec. 21, 2017

(30) Foreign Application Priority Data

Jun. 16, 2016 (JP) ................. 2016-119689

(51) Int. Cl.
*G02B 21/00* (2006.01)
*G01N 21/64* (2006.01)
*G02B 21/36* (2006.01)

(52) U.S. Cl.
CPC ..... *G02B 21/0032* (2013.01); *G01N 21/6458* (2013.01); *G02B 21/008* (2013.01); *G02B 21/0044* (2013.01); *G02B 21/365* (2013.01)

(58) Field of Classification Search
None
See application file for complete search history.

(56) References Cited

U.S. PATENT DOCUMENTS

| 6,426,835 B1 | 7/2002 | Endo et al. |
| 6,433,345 B1 | 8/2002 | Hayashi et al. |
| 6,839,134 B2 * | 1/2005 | Saito ............ G01J 3/08 250/458.1 |
| 2002/0097490 A1 | 7/2002 | Endo et al. |

(Continued)

FOREIGN PATENT DOCUMENTS

| DE | 10014331 A1 | 10/2000 |
| EP | 1067375 A2 | 1/2001 |

(Continued)

OTHER PUBLICATIONS

Extended European Search Report (EESR) dated Nov. 24, 2017 issued in counterpart European Application No. 17173275.3.

*Primary Examiner* — Jayanti K Patel
*Assistant Examiner* — Shadan E Haghani
(74) *Attorney, Agent, or Firm* — Holtz, Holtz & Volek PC (57) ABSTRACT

Provided is a scanning microscope including a pinhole array disk having a plurality of pinholes restricting a light flux of illumination light for irradiating a sample, the plurality of pinholes being disposed so as to form an array about a center axis; a rotational driving unit rotating the pinhole array disk about the center axis; an objective lens irradiating the sample with the illumination light that has passed through the pinholes and collecting fluorescence from the sample to cause the fluorescence to enter the pinholes; a camera acquiring an image of the sample by repeatedly capturing the fluorescence that has passed through the pinholes; and a stimulation optical system irradiating the sample with stimu- (Continued)

lation light, wherein the system includes a stimulation-timing generating unit decreasing the intensity of the stimulation light during exposure periods of the camera and increasing the intensity of the stimulation light during periods between exposure periods.

16 Claims, 9 Drawing Sheets

(56) References Cited

U.S. PATENT DOCUMENTS

| | | | |
|---|---|---|---|
| 2006/0050375 A1* | 3/2006 | Mikuriya | G02B 21/0044 359/385 |
| 2010/0142041 A1* | 6/2010 | Berman | G02B 21/0032 359/385 |
| 2011/0134519 A1* | 6/2011 | Cooper | G02B 21/0032 359/385 |
| 2011/0182529 A1* | 7/2011 | Kempe | G01N 21/6458 382/274 |
| 2016/0131885 A1* | 5/2016 | Nakayama | G01N 21/6428 250/458.1 |

FOREIGN PATENT DOCUMENTS

| | | |
|---|---|---|
| JP | 2001070227 A | 3/2001 |
| JP | 2006078772 A | 3/2006 |

\* cited by examiner

SCANNING MICROSCOPE

CROSS-REFERENCE TO RELATED APPLICATIONS

This application claims the benefit of Japanese Patent Application No. 2016-119689, the content of which is incorporated herein by reference.

TECHNICAL FIELD

The present invention relates to scanning microscopes.

BACKGROUND ART

In the related art, a scanning microscope of the disk scanning type is known (e.g., see Patent Literature 1), wherein a pinhole array disk having a plurality of pinholes is provided, and the pinhole array disk is rotated about a center axis so as to rapidly switch the pinholes through which laser light is passed, whereby the position of the laser light spot on a sample is moved so as to scan the laser light. With a scanning microscope of the disk scanning type, it is possible to acquire a confocal image at high speed by scanning laser light at multiple points via a plurality of pinholes.

CITATION LIST

Patent Literature

{PTL 1}
Japanese Unexamined Patent Application, Publication No. 2006-78772

SUMMARY OF INVENTION

An aspect of the present invention is a scanning microscope including an open disk having a plurality of micro-openings that restrict a light flux of illumination light for irradiating a sample, the plurality of micro-openings being disposed so as to form an array about a center axis; a rotational driving unit that rotates the open disk about the center axis; an objective lens that irradiates the sample with the illumination light that has passed through the micro-openings of the open disk being rotated about the center axis by the rotational driving unit and that collects observation light emitted at the sample and causes the observation light to enter the micro-openings; an image acquisition unit that acquires an image of the sample by repeatedly capturing the observation light that has been collected by the objective lens and that has passed through the micro-openings; and a stimulation-light irradiation unit that irradiates the sample with stimulation light, wherein the stimulation-light irradiation unit includes a light modulation unit that decreases the intensity of the stimulation light for irradiating the sample during an exposure period of the image acquisition unit and increases the intensity of the stimulation light during a period between exposure periods.

DESCRIPTION OF EMBODIMENTS

[First Embodiment]

A scanning microscope according to a first embodiment of the present invention will be described below with reference to the drawings.

Figure 1:
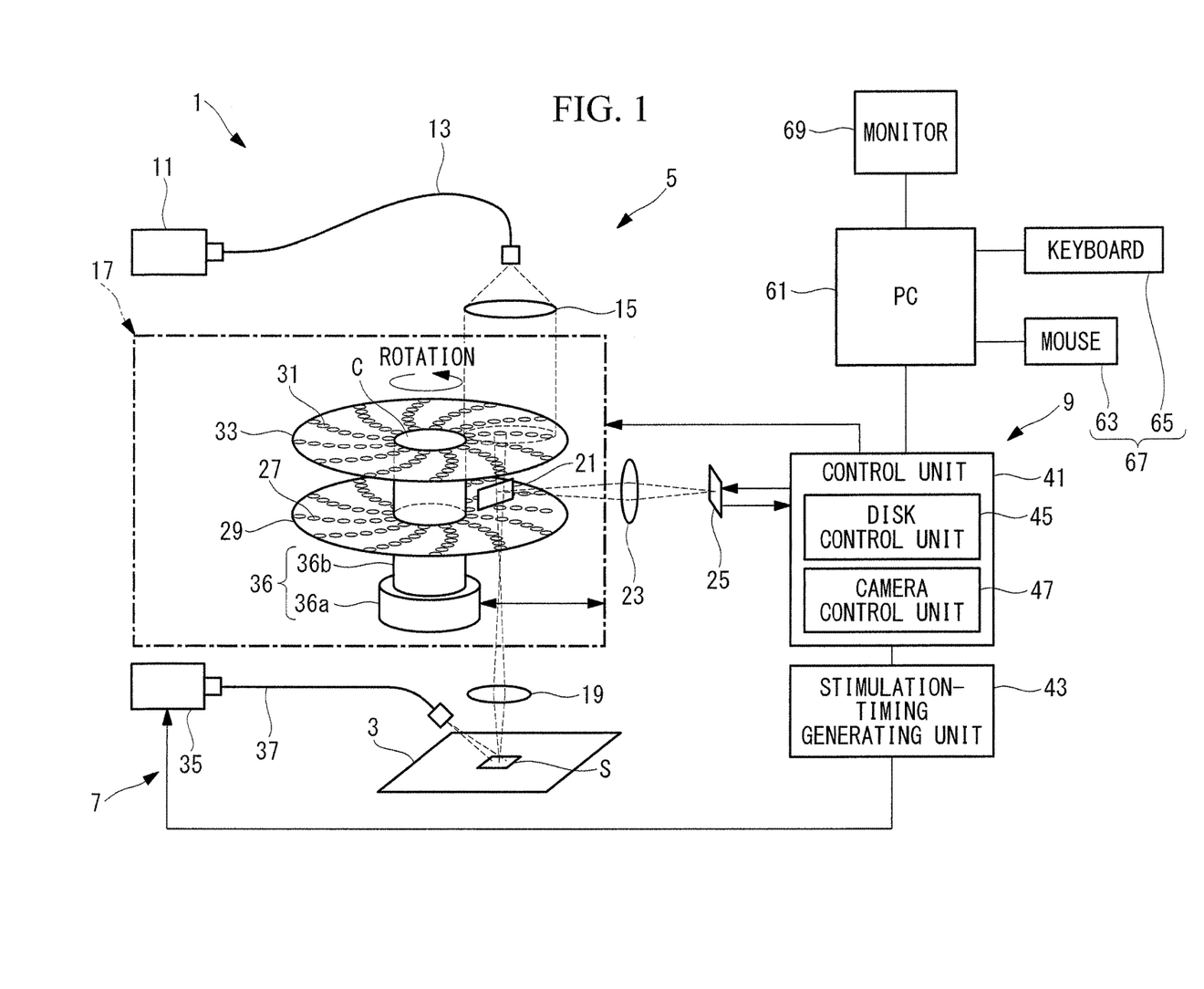
FIG. 1 schematically shows the configuration of a scanning microscope according to a first embodiment of the present invention.

As shown in FIG. 1, a scanning microscope 1 according to this embodiment includes a stage 3 on which a sample S is placed, an observation optical system 5 that acquires an image of the sample S, a stimulation optical system (stimulation light irradiation unit) 7 that irradiates the sample S with stimulation light, and a control device 9 that controls the observation optical system 5 and the stimulation optical system 7.

The observation optical system 5 includes an image formation laser light source (hereinafter referred to as an image formation light source) 11 that emits laser light that serves as illumination light, an optical fiber 13 that guides the illumination light emitted from the image formation light source 11, a collimating lens 15 that converts the illumination light guided through the optical fiber 13 into collimated light, a confocal scanner 17 that scans the illumination light converted into collimated light via the collimating lens 15, and an objective lens 19 that irradiates the sample S with the illumination light scanned by the confocal scanner 17 and that collects fluorescence (observation light) that returns from the sample S.

Furthermore, the observation optical system 5 includes a dichroic mirror 21 that causes the fluorescence collected by the objective lens 19 and returning along the optical path of the illumination light to branch from the optical path of the illumination light, an image forming lens 23 that forms an image with the fluorescence branched via the dichroic mirror 21, and a camera (image acquisition unit) 25, such as a CCD, that captures the image formed via the image forming lens 23.

The confocal scanner 17 is a disk-shaped scanner. The confocal scanner 17 includes a pinhole array disk (open disk) 29 having a plurality of pinholes (micro-openings) 27 disposed so as to form an array about a rotation axis (center axis) C, a microlens array disk 33 having a plurality of microlenses 31 disposed so as to form an array about the rotation axis C, and a rotational driving unit 36 that rotates the pinhole array disk 29 and the microlens array disk 33 about the rotation axis C.

The rotational driving unit 36 includes an interface circuit 36a that carries out communications with a disk control unit 45, which will be described later, and a DC servo motor 36b. The DC servo motor 36b includes an encoder (not shown) that can output a rotation-speed signal. Although the DC servo motor 36b is used in this embodiment, without limitation thereto, a motor that allows rate control, such as an AC servo motor, may be used.

The microlens array disk 33 and the pinhole array disk 29 are formed together with a gap therebetween in the direction along the rotation axis C, with the microlens array disk 33 disposed on the image formation light source 11 side and the microlens array disk 33 disposed on the sample S side. Furthermore, the microlens array disk 33 and the pinhole array disk 29 are configured to be rotated together about the common rotation axis C by the rotational driving unit 36.

Furthermore, in the confocal scanner 17, the pinholes 27 in the pinhole array disk 29 and the microlenses 31 on the microlens array disk 33 are formed in the same disk pattern (array pattern), with the individual pinholes 27 and the individual microlenses 31 associated with each other. Thus, illumination light that enters the microlenses 31 is collected by the pinholes 27 associated with the individual microlenses 31.

Figure 2:
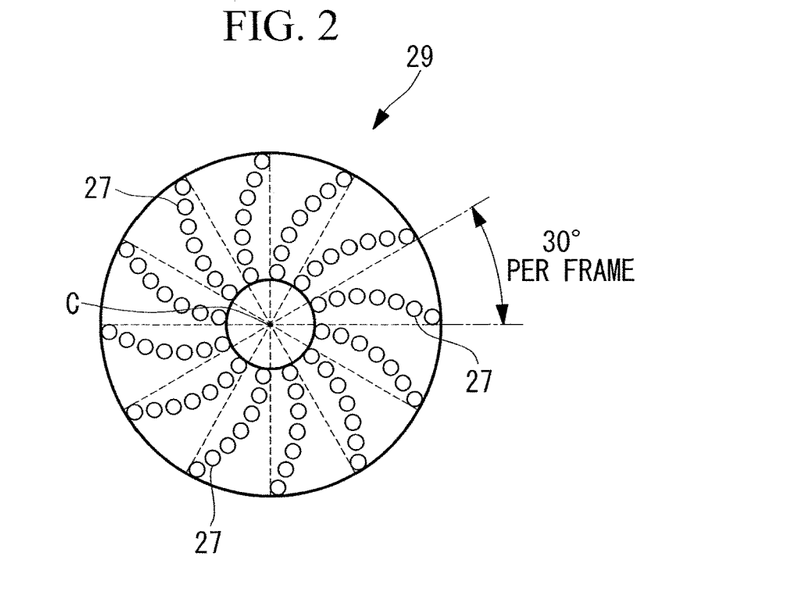
FIG. 2 is a plan view showing an example of an array of a plurality of pinholes in a pinhole array disk in FIG. 1.

In the pinhole array disk 29, for example, as shown in FIG. 2, in each fan-shaped region spanning 30° in the circumferential direction about the rotation axis C, a plurality of pinholes 27 are disposed from the center to the periphery of the pinhole array disk 29, with their positions gradually shifted in the circumferential direction. This also applies to the microlenses 31 on the microlens array disk 33. Thus, each time the pinhole array disk 29 and the microlens array disk 33 are rotated by 30° about the rotation axis C, the entire surface of the sample S, i.e., one frame of the camera 25, is scanned.

Furthermore, the individual pinholes 27 are configured to pass the illumination light collected by the associated microlenses 31 toward the sample S and to pass only the fluorescence coming from the focal point of the objective lens 19 at the sample S among the fluorescence collected by the objective lens 19 in the direction opposite to the direction of the illumination light.

The dichroic mirror 21 is disposed on the optical axis of the illumination light between the microlens array disk 33 and the pinhole array disk 29. The dichroic mirror 21 is configured to pass the illumination light collected at the associated pinholes 27 via the individual microlenses 31 and to reflect the fluorescence from the sample S, having passes through the pinholes 27, toward the image forming lens 23.

The stimulation optical system 7 includes a stimulation LED light source (hereinafter referred to as a stimulation light source) 35 that emits laser light that serves as stimulation light and an optical fiber 37 that guides the stimulation light emitted from the stimulation light source 35 to irradiate the sample S. The stimulation light source 35 is configured to allow direct light modulation using a current.

The control device 9 includes a control unit 41 that controls the confocal scanner 17 and the camera 25 and a stimulation-timing generating unit (light modulation unit) 43 that generates timing at which stimulation light is emitted from the stimulation light source 35. A personal computer (PC) 61 is connected to the control device 9. Furthermore, an input unit 67 that allows a user to enter an exposure time, etc. for the camera 25, such as a mouse 63 and a keyboard 65, and a monitor 69 are connected to the PC 61.

The control unit 41 includes a disk control unit 45 that controls the rotation speed of the rotational driving unit 36 and a camera control unit 47 that controls the exposure time of the camera 25. Furthermore, the control unit 41 includes an interface circuit (not shown) that carries out communications with the stimulation-timing generating unit 43.

The disk control unit 45 includes a drive circuit (not shown) that sends a driving signal to the rotational driving unit 36, a feedback circuit (not shown) that controls the rotation speed on the basis of a rotation-speed signal sent from the rotational driving unit 36, and a PC interface circuit (not shown) that sends and receives data to and from the PC 61. The disk control unit 45 is configured to rotate the rotational driving unit 36 at a rotation speed of 10,000 rpm.

The camera control unit 47 includes a camera interface circuit (not shown) that receives an image signal from the camera 25 and that sends an exposure signal to the camera 25, a processor (not shown) that executes various kinds of signal processing, and a PC interface circuit (not shown) that sends image information to the PC 61.

Here, it is possible to calculate the shortest exposure time Tmin for the camera 25 on the basis of the disk pattern (1 frame=30°) of the pinhole array disk 29 and the rotation speed (10,000 rpm) of the rotational driving unit 36. The number of frames that can be acquired in one revolution of the confocal scanner 17 about the rotation axis C is 360°/30°=12 frames, and the fastest frame rate is 10,000 rpm/60 s×12 frames=2000 [fps]. Thus, the shortest exposure time Tmin taken to scan one frame at this frame rate is 1/2000 [fps]=0.5 [ms].

In the control unit 41, for example, the exposure time T that can be set by the user is restricted to values not less than the shortest exposure time Tmin, and a substantially integer multiple (Tmin×N) of the shortest exposure time Tmin is set as a recommended value of the exposure time T. For example, in the case of the fastest rate, the exposure time is set to T=the shortest exposure time Tmin×1=0.5 [ms].

Figure 3:
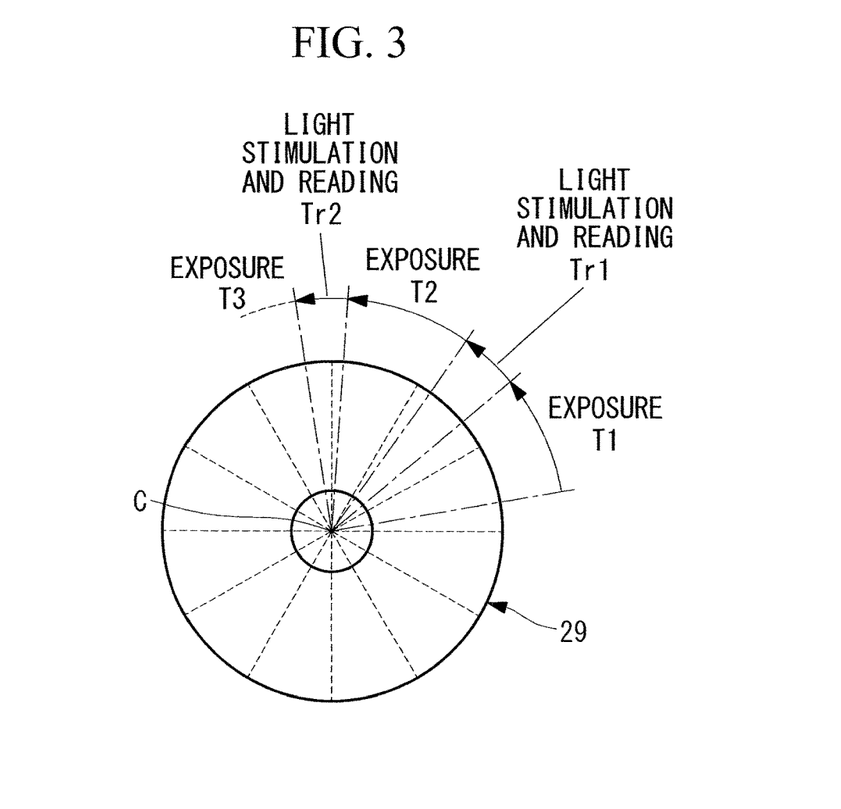
FIG. 3 is a plan view showing the relationship between the pinhole array disk in FIG. 2 and exposure periods and read periods of a camera.
Figure 4:
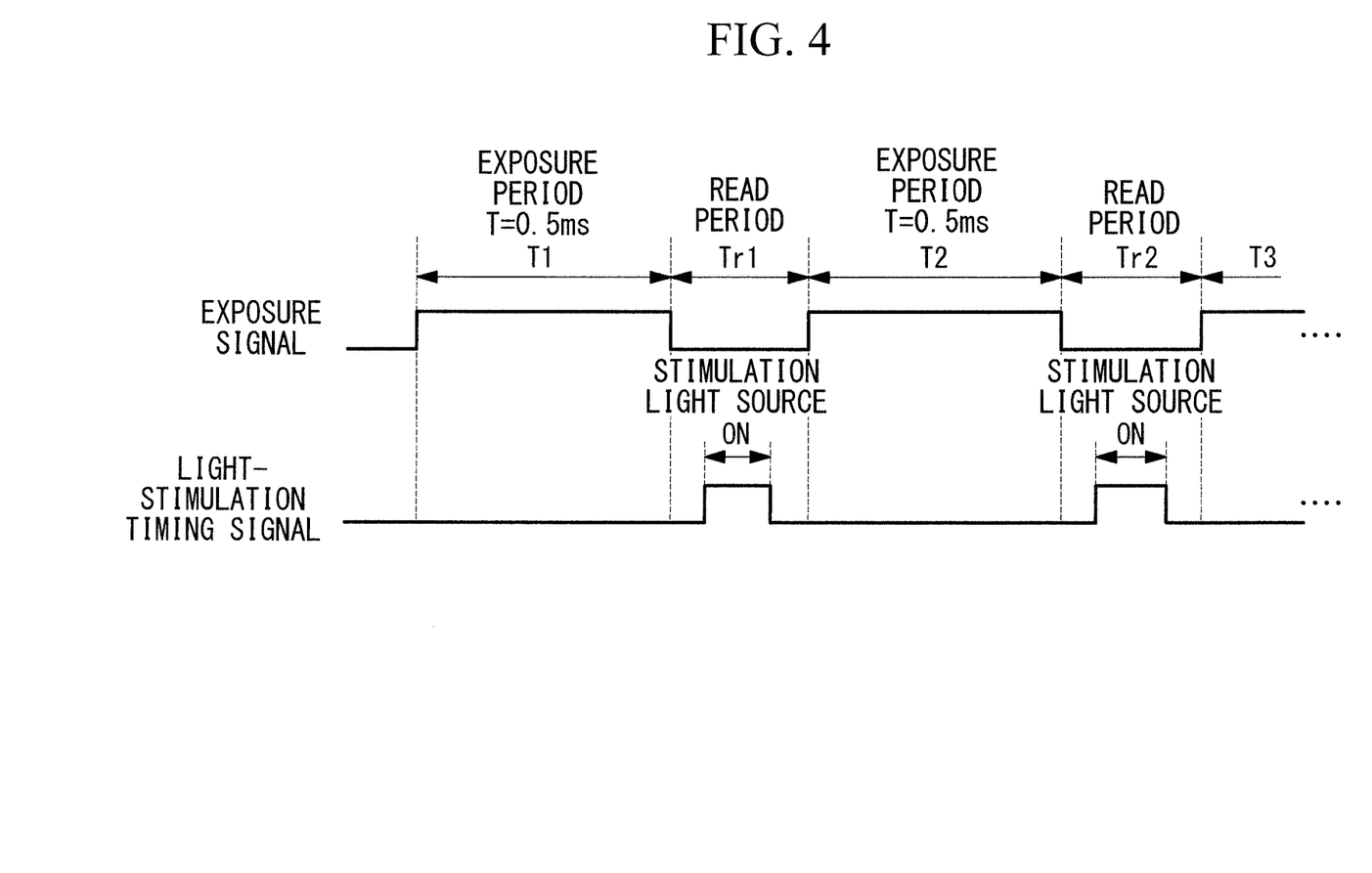
FIG. 4 is a timing chart showing an example of the relationship between the exposure periods of the camera and a light-stimulation timing signal.

The camera control unit 47 is configured to generate an exposure signal from the exposure time T set for the camera 25 by the user and the read time Tr in which image information acquired by the camera 25 is transferred to the PC 61. As shown in FIGS. 3 and 4, the exposure signal alternates between periods of the exposure time T (T1, T2, T3, . . . ) (exposure periods) and periods of the read time Tr (Tr1, Tr2, Tr3, . . . ). It is permissible to adjust the read time Tr, with its minimum value being regulated by the fastest rate defined for the camera 25. Furthermore, the camera control unit 47 is configured to drive the camera 25 on the basis of the generated exposure signal.

The stimulation-timing generating unit 43 is configured to modulate light emitted from the stimulation light source 35 on the basis of the exposure signal generated by the camera control unit 47 so as to decrease the intensity of the stimulation light for stimulating the sample S during periods of the exposure time T of the camera 25 and so as to increase the intensity of the stimulation light during periods between the periods of the exposure time T. Specifically, the stimulation-timing generating unit 43 includes a camera-control-unit interface circuit (not shown) that receives the exposure signal sent from the camera control unit 47, a stimulation-light-source interface circuit (not shown) that sends a light modulation signal to the stimulation light source 35, a central processing unit (CPU) (not shown) that converts the exposure signal sent from the camera control unit 47 into a light modulation signal for the stimulation light source 35, and a memory (not shown) in which a program for the operation of the CPU is written. Thus configured, the stimulation-timing generating unit 43 operates as a light modulation unit for the stimulation light source 35.

Specifically, as shown in FIG. 4, the stimulation-timing generating unit 43 is configured to generate a timing signal for light stimulation so as to emit stimulation light from the stimulation light source 35 (ON) in each period between periods of the exposure time T, i.e., in each period of the read time Tr, and so as to stop the emission of stimulation light from the stimulation light source 35 (OFF) in each period of the exposure time T, i.e., in each period between periods of the read time Tr, thereby switching the stimulation light source 35 ON/OFF. The timing signal for light stimulation may be any signal that allows recognition of periods of the read time Tr. For example, the timing signal for light stimulation may be generated on the basis of a signal from the camera 25 or a trigger signal for the camera 25.

Figure 5:
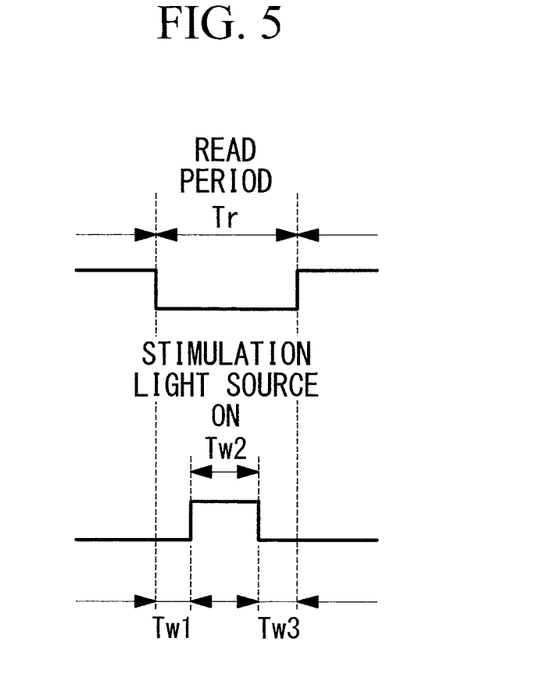
FIG. 5 is an enlarged view of a read period in the timing chart in FIG. 4.

Furthermore, the stimulation-timing generating unit 43 is configured to adjust the timing at which stimulation light is emitted from the stimulation light source 35 in periods of the read time Tr. For example, as shown in FIG. 5, the user is allowed to set a period Tw1 from the start of the read time Tr to just before the emission of stimulation light from the stimulation light source 35, a period Tw2 during which stimulation light is actually emitted from the stimulation light source 35, and a period Tw3 from the end of emission of stimulation light from the stimulation light source 35 to the end of the read time Tr.

Preferably, these periods Tw1, Tw2, and Tw3 should be set in consideration of delays associated with activation and deactivation of the stimulation light source 35 such that stimulation light is emitted from the stimulation light source 35 only in periods of the read time Tr. This makes it possible to efficiently irradiate the sample S with stimulation light having high intensity from the stimulation light source 35, while avoiding the effect of the stimulation light on the image information.

The operation of the thus-configured scanning microscope 1 will now be described.

In the case where a sample S is stimulated with light and the resulting response is observed by using the scanning microscope 1 according to this embodiment, first, by using the input unit 67, the user sets the exposure time T of the camera 25 and the periods Tw1, Tw2, and Tw3 relating to the emission of stimulation light during periods of the read time Tr. For example, the exposure time T=0.5 ms. Then, in the observation optical system 5, the rotational driving unit 36 rotates the confocal scanner 17 about the rotation axis C, and the image-formation light source 11 emits illumination light.

The illumination light emitted from the image-formation light source 11 is guided through the optical fiber 13, is converted into collimated light via the collimating lens 15, and enters the confocal scanner 17. The illumination light that has entered the confocal scanner 17 is collected by the microlenses 31 disposed on the optical path of the illumination light, passes through the dichroic mirror 21, passes through the pinholes 27 also disposed on the optical path of the illumination light, and irradiates the sample S via the objective lens 19.

As the microlenses 31 and the pinholes 27 through which the illumination light passes change rapidly in accordance with the rotation of the confocal scanner 17, the position of the spot of the illumination light on the sample S is moved according to the pattern of the microlenses 31 and the pinholes 27, whereby the illumination light is scanned over the sample S.

The fluorescence generated at the sample S irradiated with the illumination light is collected by the objective lens 19, returns along the optical path of the illumination light, passes through the pinholes 27, and is reflected by the dichroic mirror 21 toward the image forming lens 23. Then, the fluorescence forms an image via the image forming lens 23 and is captured by the camera 25. Thus, image information for the sample S, based on the captured fluorescence, is acquired by the camera 25.

Next, in the case where the sample S is stimulated with light by using the scanning microscope 1 according to this embodiment, in the stimulation optical system 7, the stimulation light source 35 emits stimulation light having a higher intensity than the illumination light, and the sample S is irradiated with the stimulation light via the optical fiber 37, whereby the sample S is stimulated with light.

As described above, by acquiring image information for the sample S by means of the observation optical system 5 and by stimulating the sample S with light by means of the stimulation optical system 7, the user can observe the response of the sample S to the light stimulus while viewing the sample S on the monitor 69, etc.

In this case, the camera control unit 47 controls the camera 25 on the basis of an exposure signal generated from the exposure time T set by the user and the read time Tr of the camera 25 so that periods of the exposure time (T1, T2, T3, . . . ) and periods of the read time (Tr1, Tr2, Tr3, . . . ) alternate, as shown in FIGS. 3 and 4. Then, the camera 25 captures the fluorescence from the sample S during a period of the exposure time T and transfers the image information to the PC 61 during a period of the read time Tr.

Furthermore, the stimulation-timing generating unit 43 modulates light emitted from the stimulation light source 35 on the basis of a light-stimulation timing signal generated from the exposure signal of the camera control unit 47, whereby the emission of stimulation light from the stimulation light source 35 is stopped (OFF) during periods of the exposure time T of the camera 25, and stimulation light is emitted from the stimulation light source 35 (ON) during periods of the read time Tr of the camera 25.

Thus, it is possible to prevent stimulation light having high intensity from entering the camera 25 when image information is being acquired by the camera 25 during exposure periods of the camera 25. Accordingly, with the scanning microscope 1 according to this embodiment, it is possible to prevent the effect of stimulation light having high intensity from being superimposed on image information. This makes it possible to precisely observe the response of the sample S to a light stimulus.

This embodiment can be modified as follow.

Figure 6:
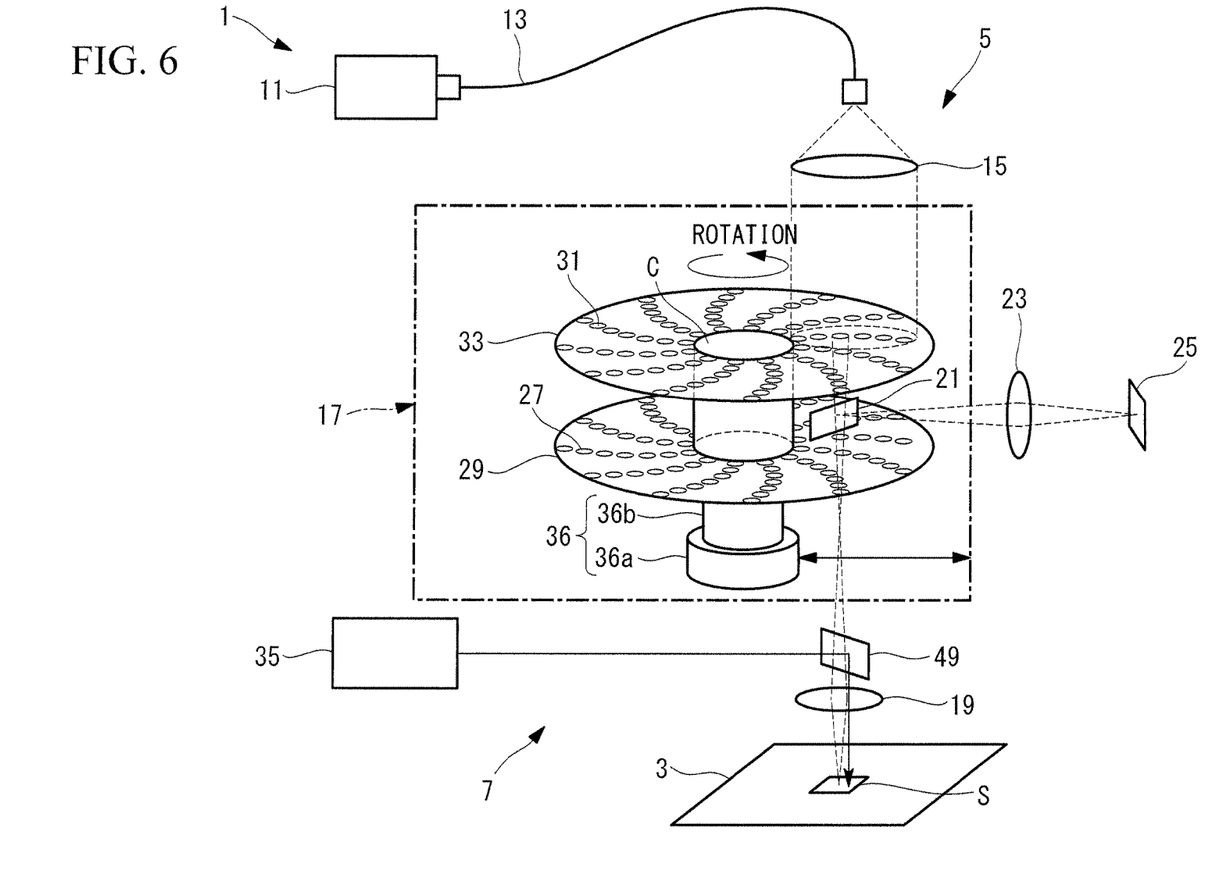
FIG. 6 schematically shows the configuration of a scanning microscope according to a modification of the first embodiment of the present invention.

For example, as shown in FIG. 6, the scanning microscope 1 may include, instead of the optical fiber 37, a dichroic mirror (optical-path combining unit) 49 that combines the optical path of the illumination light and the optical path of the stimulation light.

In this case, the dichroic mirror 49 should be disposed on the optical path of the illumination light and the fluorescence between the confocal scanner 17 and the objective lens 19. Furthermore, the dichroic mirror 49 should be configured to pass the illumination light from the image-formation light source 11 and the fluorescence from the sample S and to reflect the stimulation light emitted from the stimulation light source 35 toward the objective lens 19.

With this configuration, the dichroic mirror 49 makes it possible to efficiently irradiate, with stimulation light, the observation range of the sample S irradiated with illumination light. This makes it possible to observe the direct response of the sample S to a light stimulus.

In this modification, a scanning unit, such as a galvanometer scanner, that scans the stimulation light emitted from the stimulation light source 35 over the sample S may be provided.

[Second Embodiment]

Next, a scanning microscope according to a second embodiment of the present invention will be described.

Figure 7:
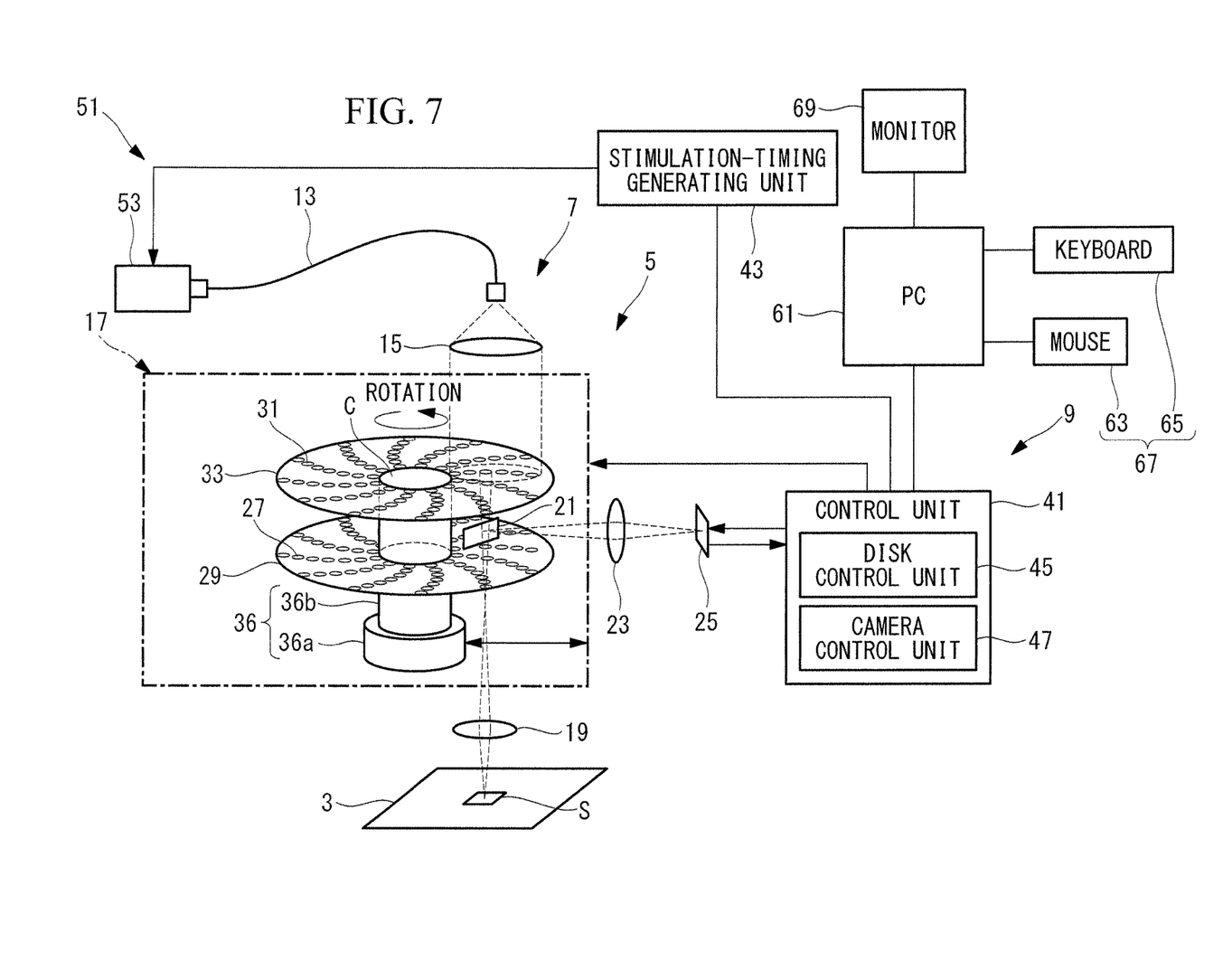
FIG. 7 schematically shows the configuration of a scanning microscope according to a second embodiment of the present invention.

As shown in FIG. 7 scanning microscope 51 according to this embodiment differs from the first embodiment in that it includes a laser light source 53 that is capable of selectively emitting illumination light and stimulation light having different wavelengths, instead of the image-formation light source 11, the optical fiber 37, and the stimulation light source 35.

Hereinafter, parts that are configured the same as those in the scanning microscope 1 according to the first embodiment are designated by the same reference signs, and descriptions thereof will be omitted.

The laser light source 53 is configured to selectively emit laser light having different wavelengths. Similarly to the illumination light emitted from the image-formation light source 11 in the first embodiment, illumination light and stimulation light emitted from the laser light source 53 are guided through the optical fiber 13, are converted into collimated light via the collimating lens 15, and irradiate the sample S via the confocal scanner 17 and the objective lens 19. Furthermore, light emitted from the laser light source 53 is modulated by the stimulation-timing generating unit 43 on the basis of a light-stimulation timing signal.

Figure 8:
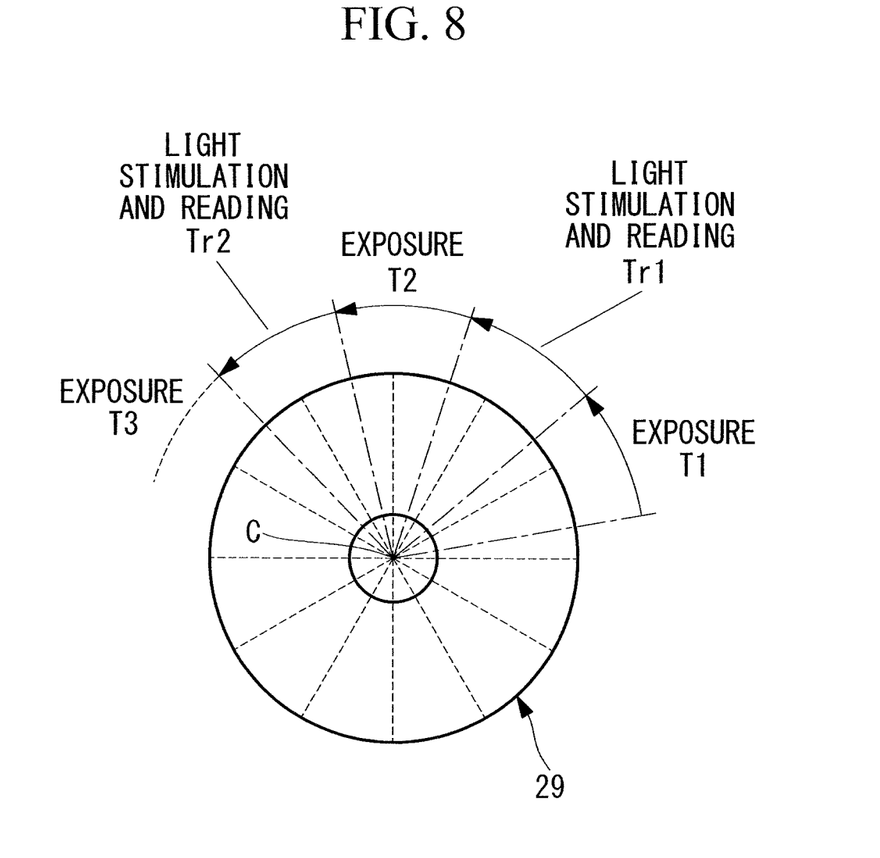
FIG. 8 is a plan view showing the relationship between a pinhole array disk in FIG. 7 and exposure periods and read periods of a camera.
Figure 9:
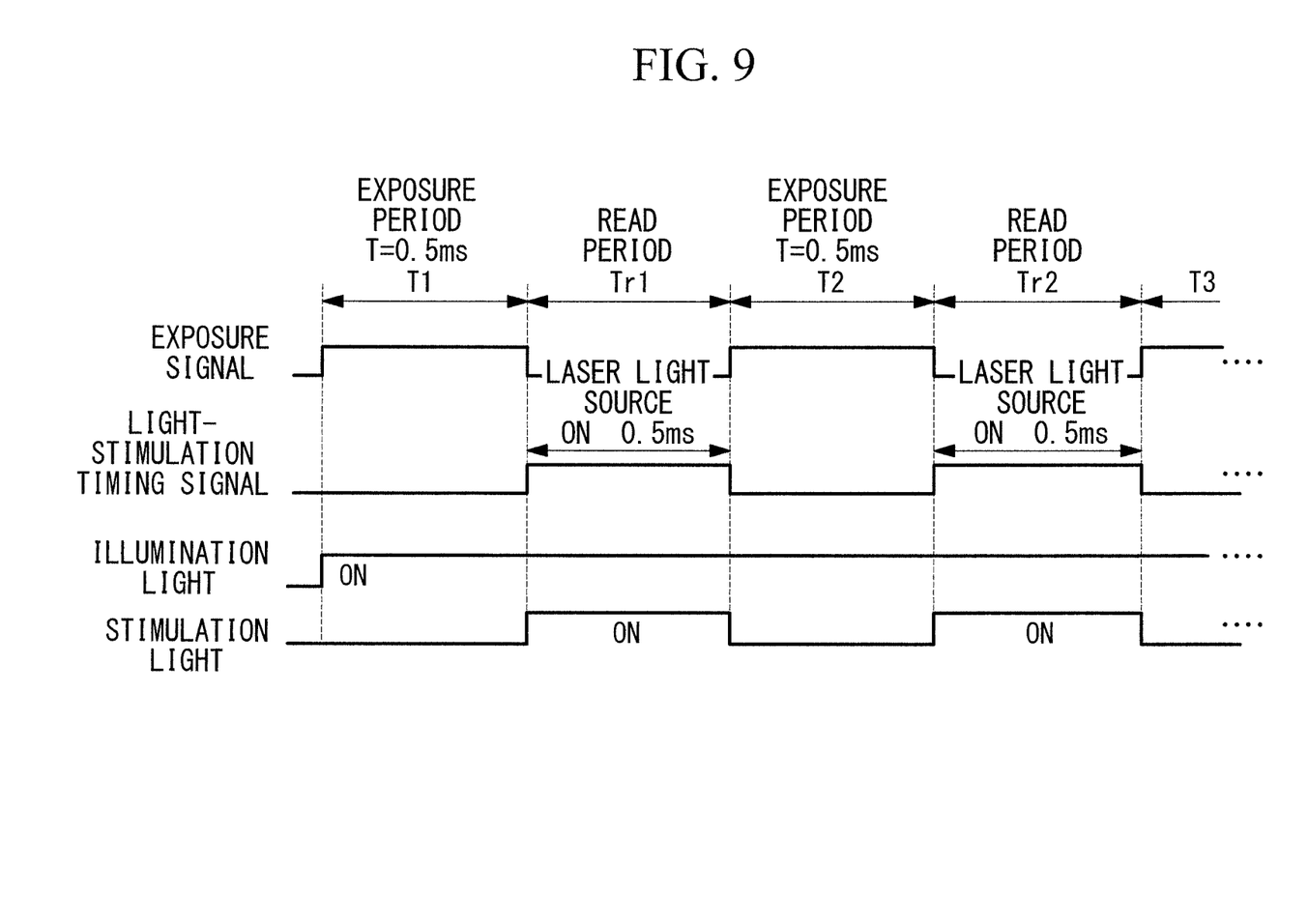
FIG. 9 is a timing chart showing an example of the relationship among the exposure periods of the camera, a light-stimulation timing signal, ON/OFF states of illumination light, and ON/OFF states of stimulation light.
Figure 10:
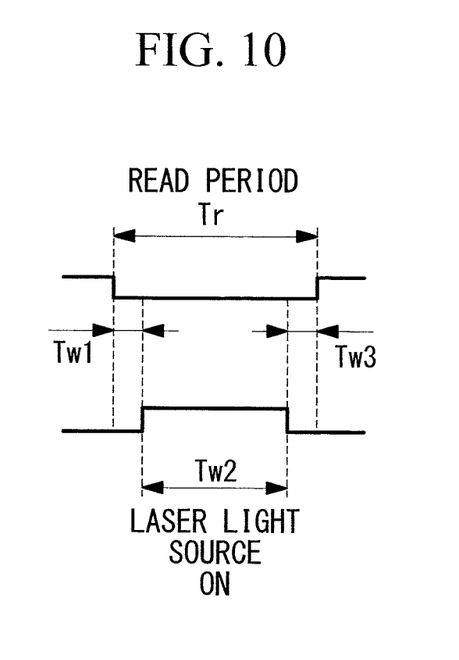
FIG. 10 is an enlarged view of the read periods in the timing chart in FIG. 9.

The camera control unit 47 is configured to generate an exposure signal from the exposure time T of the camera 25, set by the user via the input unit 67, and the read time Tr of the camera 25, where the read time Tr of the camera 25≥the shortest exposure time Tmin. The exposure signal alternates between periods of the exposure time T and periods of the read time Tr, as shown in FIGS. 8 and 9. As the read time Tr, which is not less than the shortest exposure time Tmin, a substantially integer multiple of the shortest exposure time Tmin is set as a recommended value, and adjustment by the user is allowed.

The stimulation-timing generating unit 43 is configured to generate a light-stimulation timing signal on the basis of an exposure signal generated by the camera control unit 47, such that, for example, as shown in FIG. 9, the laser light source 53 emits stimulation light having a higher intensity than illumination light during periods of the read time Tr (stimulation periods) having a length not less than a scanning time taken for scanning one frame at the frame rate, as calculated on the basis of the disk pattern of the pinhole array disk 29 and the rotation speed of the rotational driving unit 36.

Furthermore, the stimulation-timing generating unit 43 is configured to allow the user to set periods Tw1, Tw2, and Tw3 during periods of the read time Tr, where Tw1 signifies a period from the start of the read time Tr to just before the emission of stimulation light from the stimulation light source 35, Tw2 signifies a period during which the stimulation light source 35 is actually emitting stimulation light, and Tw3 signifies a period from the end of emission of stimulation light from the stimulation light source 35 to the end of the read time Tr.

The operation of the thus-configured scanning microscope 51 will now be described.

In the case where a sample S is stimulated with light and the resulting response is observed by using the scanning microscope 51 according to this embodiment, first, by using the input unit 67, the user sets the exposure time T of the camera 25 and the periods Tw1, Tw2, and Tw3 relating to the emission of stimulation light during periods of the read time Tr. Then, the rotational driving unit 36 rotates the confocal scanner 17 about the rotation axis C, and the laser light source 53 emits illumination light. For example, the exposure time T=0.5 ms, and the read time Tr=0.5 ms. Hereinafter, a description of the acquisition of image information for the sample S will be omitted since it is the same as in the first embodiment.

Next, in the case where the sample S is stimulated with light, the laser light source 53 emits stimulation light having a higher intensity instead of the illumination light, while the confocal scanner 17 continues to be rotated about the rotation axis C. Similarly to the illumination light, the stimulation light emitted from the laser light source 53 is guided through the optical fiber 13, is converted into collimated light via the collimating lens 15, then passes through the confocal scanner 17, and irradiates the sample S via the objective lens 19. Thus, similarly to the illumination light, the stimulation light is scanned over the sample S in accordance with the disk pattern of the confocal scanner 17.

As described above, by acquiring image information for the sample S with the common laser light source 53 by means of the observation optical system 5 and by stimulating the sample S with light by means of the stimulation optical system 7, the user can observe the response of the sample S to the light stimulus while viewing the sample S on the monitor 69, etc.

In this case, the camera control unit 47 controls the camera 25 on the basis of an exposure signal generated from the exposure time T set by the user and the read time Tr of the camera 25 so that periods of the exposure time (T1, T2, . . . ) and periods of the read time (Tr1, Tr2, . . . ) alternate, as shown in FIGS. 8 and 9. Then, the camera 25 captures the fluorescence from the sample S during a period of the exposure time T and transfers the image information to the PC 61 during a period of the read time Tr.

Furthermore, the stimulation-timing generating unit 43 modulates light emitted from the laser light source 53 on the basis of a light-stimulation timing signal generated from the exposure signal of the camera control unit 47, whereby the emission of stimulation light from the laser light source 53 is stopped (OFF) during periods of the exposure time T of the camera 25, and stimulation light is emitted from the laser light source 53 (ON) during periods of the read time Tr of the camera 25. This prevents stimulation light having high intensity from entering the camera 25 while image information is being acquired by the camera 25.

As described above, with the scanning microscope 51 according to this embodiment, illumination light and stimulation light are emitted from the common laser light source 53, which enables a compact and simple implementation of the scanning microscope 51. Furthermore, since the sample S is irradiated with stimulation light having high intensity by the confocal scanner 17 and the stimulation-timing generating unit 43, in each range corresponding to one frame at the frame rate calculated on the basis of the disk pattern of the pinhole array disk 29 and the rotation speed of the rotational driving unit 36, it is possible to observe the response of the sample S in the case where the entire observation range is stimulated with light.

Although the embodiments of the present invention have been described above in detail with reference to the drawings, specific configurations of the present invention are not limited to those in the embodiments, and the present invention includes design modifications, etc. within the scope thereof. For example, without limitation to application to the above embodiments and modifications, the present invention may be applied to embodiments in which the above embodiments and modifications are combined as appropriate, without any particular limitation.

Furthermore, although the stimulation-timing generating unit 43 stops the emission of stimulation light during periods of the exposure time T in the above embodiments, alternatively, for example, the stimulation-timing generating unit 43 may decrease the intensity of the stimulation light to not greater than a predetermined threshold during periods of the exposure time T. For example, the stimulation-timing generating unit 43 may be configured such that normal stimulation light having higher intensity than illumination light is emitted from the stimulation light source 35 or the laser light source 53 during each period between periods of the exposure time T and such that stimulation light having an intensity not greater than the predetermined threshold is emitted from the stimulation light source 35 or the laser light source 53 during each period of the exposure time T.

For example, the predetermined threshold may be set to be a maximum value of intensity with which the sample S is not stimulated even when irradiated with stimulation light. Also in this case, even if stimulation light enters the camera 25, the effect of the stimulation light on the image information can be suppressed. The above configuration is effective in a case where, if the emission of stimulation light from the stimulation light source 35 or the laser light source 53 is stopped, it takes time to reactivate the stimulation light source 35 or the laser light source 53, and thus it is not possible to emit stimulation light having high intensity at the desired timing.

Furthermore, although light emitted from the stimulation light source 35 or the laser light source 53 is directly modulated in the above embodiments, alternatively, for example, an acousto-optic element may be adopted to modulate the stimulation light emitted from the stimulation light source 35 or the laser light source 53. Alternatively, an optical chopper or shutter may be disposed on the optical path of stimulation light emitted from the stimulation light source 35, and it is acceptable to switch between emission (ON) and stopping (OFF) of stimulation light by opening and closing the optical path by means of the optical chopper or shutter. In this case, the driving of the optical chopper or shutter can be controlled by the stimulation-timing generating unit 43.

Furthermore, although stimulation light is emitted from the stimulation light source 35 or the laser light source 53 in each period of the read time Tr in the above embodiments, alternatively, stimulation light may be emitted from the stimulation light source 35 or the laser light source 53 only during a period of the read time Tr among a plurality of periods of the read time Tr, or stimulation light may be emitted from the stimulation light source 35 or the laser light source 53 only during some chosen periods of the read time Tr.

Furthermore, although the pinholes 27 and the microlenses 31 are disposed such that scanning for one frame at the frame rate takes place each time the confocal scanner 17 is rotated by 30° about the rotation axis C in the above embodiments, without limitation to the embodiments, for example, the pinholes 27 and the microlenses 31 may be disposed such that scanning for one frame at the frame rate takes place each time the confocal scanner 17 is rotated about the rotation axis C by an angle other than 30°, such as 15°, 45°, or 60°.

Furthermore, although an LED is used as the stimulation light source 35 as an example in the above embodiments, alternatively, for example, a laser or a mercury light source may be adopted as the stimulation light source 35.

From the above-described embodiment, the following invention is derived.

An aspect of the present invention is a scanning microscope including an open disk having a plurality of micro-openings that restrict a light flux of illumination light for irradiating a sample, the plurality of micro-openings being disposed so as to form an array about a center axis; a rotational driving unit that rotates the open disk about the center axis; an objective lens that irradiates the sample with the illumination light that has passed through the micro-openings of the open disk being rotated about the center axis by the rotational driving unit and that collects observation light emitted at the sample and causes the observation light to enter the micro-openings; an image acquisition unit that acquires an image of the sample by repeatedly capturing the observation light that has been collected by the objective lens and that has passed through the micro-openings; and a stimulation-light irradiation unit that irradiates the sample with stimulation light, wherein the stimulation-light irradiation unit includes a light modulation unit that decreases the intensity of the stimulation light for irradiating the sample during an exposure period of the image acquisition unit and increases the intensity of the stimulation light during a period between exposure periods.

According to this aspect, the open disk is rotated about the center axis by the rotational driving unit, whereby the micro-openings through which the illumination light passes are rapidly switched in accordance with the array pattern thereof. Thus, the position of the spot of the illumination light is moved so as to scan the illumination light over the sample. Then, observation light that has been emitted at the sample scanned with the illumination light and that has passed through the micro-openings via the objective lens is repeatedly captured by the image acquisition unit, whereby an image of the sample is acquired. Furthermore, the stimulation-light irradiation unit irradiates the sample with stimulation light to apply a light stimulus to the sample. Accordingly, by acquiring, by means of the image acquisition unit, an image of the sample that has been stimulated with light by the stimulation-light irradiation unit, it becomes possible to observe the response of the sample to the light stimulus.

In this case, by using the light modulation unit of the stimulation-light irradiation unit to adjust the intensity of stimulation light in accordance with the exposure periods of the image acquisition unit such that the intensity of stimulation light is decreased during the exposure periods, it is possible to prevent stimulation light having high intensity from entering the image acquisition unit while the image acquisition unit is acquiring an image. This prevents the effect of the stimulation light having high intensity from being superimposed on image information, which enables precise observation of the response of the sample to the light stimulus.

In the above aspect, the light modulation unit may stop the irradiation with the stimulation light or decrease the intensity of the stimulation light to not greater than a predetermined threshold during the exposure period.

With this configuration, in the case where the irradiation with the stimulation light is stopped, the stimulation light is prevented from entering the image acquisition unit, and in the case where the intensity of the stimulation light is decreased to not greater than the predetermined threshold, even if the stimulation light enters the image acquisition unit, the effect of the stimulation light on image information can be suppressed. This serves to more reliably prevent the effect of the stimulation light from being superimposed on the image information.

In the above aspect, the exposure period of the image acquisition unit may have a length not less than a scanning time taken for scanning one frame at a frame rate that is calculated on the basis of an array pattern of the micro-openings and a rotation speed of the rotational driving unit.

With this configuration, it is possible to acquire an image of the sample over the entire scanning range of the illumination light by repeatedly capturing, by means of the image acquisition unit, the observation light from the sample for not less than one frame at the frame rate, i.e., the frame rate that is calculated on the basis of the array pattern of the micro-openings and the rotation speed of the rotational driving unit.

In the above aspect, the length of the exposure period may be set to be substantially an integer multiple of the scanning time.

With this configuration, it is possible to acquire an image of the sample over the entire scanning range of the illumination light by repeatedly capturing, by means of the image acquisition unit, the observation light from the sample per plurality of frames at the frame rate.

In the above aspect, the scanning microscope may further include an optical-path combining unit that combines an optical path of the illumination light and an optical path of the stimulation light.

With this configuration, it is possible with the optical-path combining unit to efficiently irradiate with the stimulation light the observation range of the sample that is irradiated with the illumination light. This enables observation of the direct response of the sample to a light stimulus.

In the above aspect, the stimulation light may irradiate the sample through the micro-openings of the open disk being rotated about the center axis by the rotational driving unit, and the light modulation unit may increase the intensity of the stimulation light during a stimulation period having a length not less than a scanning time taken for scanning one frame at a frame rate that is calculated on the basis of an array pattern of the micro-openings and a rotation speed of the rotational driving unit.

With this configuration, by adopting a common light source for illumination light and stimulation light, a compact and simple implementation of the microscope becomes possible. In this case, since the sample is irradiated with the stimulation light having high intensity by the open disk and the light modulation unit in each range corresponding to at least one frame at the frame rate, it is possible to observe the response of the sample in the case where the entire observation range is stimulated with light.

In the above aspect, the length of the stimulation period may be set to be substantially an integer multiple of the scanning time.

With this configuration, it is possible to apply, by means of the light modulation unit, a light stimulus in each range corresponding to a plurality of frames at the frame rate.

In the above aspect, the light modulation unit may allow adjustment of the timing at which the intensity of the stimulation light is increased during a period between exposure periods.

With this configuration, it is possible to efficiently increase the intensity of the stimulation light when irradiating the sample, while considering a delay between the start of a change in the intensity of the stimulation light and the completion of the change and avoiding the effect of the stimulation light on image information.

REFERENCE SIGNS LIST 1, 51 Scanning microscopes
7 Stimulation optical system (stimulation-light irradiation unit)
19 Objective lens
25 Camera (image acquisition unit)
27 Pinholes (micro-openings)
29 Pinhole array disk (open disk)
36 Rotational driving unit
43 Stimulation-timing generating unit (light modulation unit)
49 Dichroic mirror (optical-path combining unit)
S Sample

The invention claimed is:

1. A scanning microscope comprising:
an open disk having a plurality of micro-openings that restrict a light flux of illumination light for irradiating a sample, the plurality of micro-openings being disposed so as to form an array about a center axis;
a rotational driving unit that rotates the open disk about the center axis;
an objective lens that irradiates the sample with the illumination light that has passed through the micro-openings of the open disk being rotated about the center axis by the rotational driving unit and that collects observation light emitted at the sample and causes the observation light to enter the micro-openings;
an image acquisition unit that acquires an image of the sample by repeatedly capturing the observation light that has been collected by the objective lens and that has passed through the micro-openings; and
a stimulation-light irradiation unit that irradiates the sample with stimulation light,
wherein the stimulation-light irradiation unit includes a light modulation unit that decreases an intensity of the stimulation light for irradiating the sample during an exposure period of the image acquisition unit and increases the intensity of the stimulation light during a read period in which image information is read out from the image acquisition unit, and
wherein the read period is adjustable.

2. The scanning microscope according to claim 1, wherein the light modulation unit stops the irradiation with the stimulation light or decreases the intensity of the stimulation light to not greater than a predetermined threshold during the exposure period.

3. The scanning microscope according to claim 1, wherein the exposure period of the image acquisition unit has a length not less than a scanning time taken for scanning one frame at a frame rate that is calculated based on an array pattern of the micro-openings and a rotation speed of the rotational driving unit.

4. The scanning microscope according to claim 3, wherein the length of the exposure period is set to be substantially an integer multiple of the scanning time.

5. The scanning microscope according to claim 1, further comprising an optical-path combining unit that combines an optical path of the illumination light and an optical path of the stimulation light.

6. The scanning microscope according to claim 1, wherein the stimulation light irradiates the sample through the micro-openings of the open disk being rotated about the center axis by the rotational driving unit, and wherein the light modulation unit increases the intensity of the stimulation light during a stimulation period having a length not less than a scanning time taken for scanning one frame at a frame rate that is calculated based on an array pattern of the micro-openings and a rotation speed of the rotational driving unit.

7. The scanning microscope according to claim 6, wherein the length of the stimulation period is set to be substantially an integer multiple of the scanning time.

8. The scanning microscope according to claim 1, wherein a timing at which the intensity of the stimulation light is increased during the read period is adjustable.

9. A scanning microscope comprising:
an open disk having a plurality of micro-openings that restrict a light flux of illumination light for irradiating a sample, the plurality of micro-openings being disposed so as to form an array about a center axis;
a motor that rotates the open disk about the center axis;
an objective lens that irradiates the sample with the illumination light that has passed through the micro-openings of the open disk being rotated about the center axis by the motor and that collects observation light emitted at the sample and causes the observation light to enter the micro-openings;
a camera that acquires an image of the sample by repeatedly capturing the observation light that has been collected by the objective lens and that has passed through the micro-openings;
a stimulation optical system comprising a stimulation light source that emits stimulation light and an optical fiber that irradiates the sample with the stimulation light; and
a light modulation unit comprising circuitry and a hardware processor, the light modulation unit being configured to decrease an intensity of the stimulation light from the stimulation optical system during an exposure period of the camera and to increase the intensity of the stimulation light from the stimulation optical system during a read period in which image information is read out from the camera,
wherein the read period is adjustable.

10. The scanning microscope according to claim 9, wherein the light modulation unit is configured to stop the irradiation with the stimulation light from the stimulation optical system or to decrease the intensity of the stimulation light from the stimulation optical system to not greater than a predetermined threshold during the exposure period.

11. The scanning microscope according to claim 9, wherein the exposure period of the camera has a length not less than a scanning time taken for scanning one frame at a frame rate that is calculated based on an array pattern of the micro-openings and a rotation speed of the motor.

12. The scanning microscope according to claim 11, wherein the length of the exposure period is set to be substantially an integer multiple of the scanning time.

13. The scanning microscope according to claim 9, further comprising a dichroic mirror that combines an optical path of the illumination light and an optical path of the stimulation light.

14. The scanning microscope according to claim 9, wherein the stimulation light from the stimulation optical system irradiates the sample through the micro-openings of the open disk being rotated about the center axis by the motor, and
wherein the light modulation unit is configured to increase the intensity of the stimulation light from the stimulation optical system during a stimulation period having a length not less than a scanning time taken for scanning one frame at a frame rate that is calculated based on an array pattern of the micro-openings and a rotation speed of the motor.

15. The scanning microscope according to claim 14, wherein the length of the stimulation period is set to be substantially an integer multiple of the scanning time.

16. The scanning microscope according to claim 9, wherein a timing at which the intensity of the stimulation light from the stimulation optical system is increased during the read period is adjustable.

* * * * *